US012600951B2

(12) United States Patent
Benton et al.

(10) Patent No.: US 12,600,951 B2
(45) Date of Patent: Apr. 14, 2026

(54) SYSTEMS AND METHODS FOR CONTINUOUS CULTIVATION AND RECOVERY OF COMESTIBLE NON-HUMAN ANIMAL CELLS

(71) Applicant: Upside Foods, Inc., Berkeley, CA (US)

(72) Inventors: Charles Knight Benton, Berkeley, CA (US); Kesav Timiri Venkat Reddy, Oakland, CA (US)

(73) Assignee: Upside Foods, Inc., Emeryville, CA (US)

( * ) Notice: Subject to any disclaimer, the term of this patent is extended or adjusted under 35 U.S.C. 154(b) by 0 days.

(21) Appl. No.: 18/742,810

(22) Filed: Jun. 13, 2024

(65) Prior Publication Data

US 2025/0382576 A1     Dec. 18, 2025

(51) Int. Cl.
*C12N 5/077* (2010.01)
(52) U.S. Cl.
CPC .................................. *C12N 5/0652* (2013.01)
(58) Field of Classification Search
None
See application file for complete search history.

(56) References Cited

U.S. PATENT DOCUMENTS

| | | | |
|---|---|---|---|
| 7,901,937 B2 | 3/2011 | Srienc et al. | |
| 2005/0095700 A1 | 5/2005 | Budzowski et al. | |
| 2008/0178739 A1* | 7/2008 | Lewnard ................ | C12M 21/02 |
| | | | 435/257.1 |
| 2022/0195359 A1 | 6/2022 | Lavon et al. | |
| 2022/0400716 A1* | 12/2022 | Rease ..................... | A23L 13/10 |
| 2024/0010709 A1* | 1/2024 | Hundley ............... | B04B 5/0442 |

OTHER PUBLICATIONS

Allman, INFORS HT, Continuous culture for beginners, published Feb. 26, 2020, 8 pages, retrieved from the internet: https://infors-ht.com/en/blog/continuous-culture-for-beginners (Year: 2020).*
Stanbury et al., Principles of Fermentation Technology (Third Edition, 2017), Design of a fermenter, Chapter 7, pp. 401-485 ( Year: 2017).*
Marenghi et al., Cytiva, The role of perfusion in maintaining high density T-cell cultures, published Apr. 2014 (Year: 2014).*
Specht et al., Biochemical Engineering Journal 132 (2018) 161-168 (Year: 2018).*
AlfaLaval CultureOne Primo, Separation system for single use processing, retrieved from the internet (Jun. 27, 2025): https://www.
alfalaval.com/globalassets/documents/products/separation/biopharma/product_leaflet_cultureone_primo_separator_and_system_en-2.pdf (Year: 2025).*
David Humbird, "Scale-up economics for cultured meat", Biotechnology Bioengineering. 118, 3239-3250. (May 30, 2021) https://doi.org/10.1002/bit.27848.
Jaap M. Schrickx, et al., "Growth and product formation in chemostat and recycling cultures by Aspergillus niger N402 and a glucoamylase overproducing transformant, provided with multiple copies of the glaA gene", Journal of General Microbiology, 139, 2801-2810. (Nov. 1, 1993) https://doi.org/10.1099/00221287-139-11-2801.
Oscar van Mastrigt, Reinier A. Egas, Søren K. Lillevang, Tjakko Abee & Eddy J. Smid, "Application of a partial cell recycling chemostat for continuous production of aroma compunds at near-zero growth rates", BMC Research Notes, 12, 173 (Mar. 25, 2019). https://doi.org/10.1186/s13104-019-4213-4.
S.J. Pirt and W.M. Kurowski, "An Extension of the Theory of the Chemostat with Feedback of Organisms. Its Experimental Realization with a Yeast Culture", Journal of General Microbiology, 63, 357-366 (Nov. 1, 1970) https://doi.org/10.1099/00221287-63-3-357.
Olguin. Membrane-based continuous fermentation with cell recycling for propionic acid production from glycerol by Acidipropionibacterium acidipropionici 1-10. Microbial Cell Factories. Web. Mar. 4, 2023; <p. 2, 2nd column, 5th paragraph, p. 6, 2nd column, 1st paragraph, p. 7, 1st column, 3rd paragraph, 2nd column, 1st paragraph>; <DOI:10.1186/s12934-023-02049-7>.
Santos, "Putting the Spotlight Back on Plant Suspension Cultures" 1-12. Web. Mar. 10, 2016; <p. 8, 1st column, 2nd paragraph>; <DOI: 10.3389/fpls.2016.00297>.
International Search Report and Written Opinion as received in PCT/US2024/033952 dated Sep. 11, 2024.

* cited by examiner

*Primary Examiner* — Evelyn Y Pyla
(74) *Attorney, Agent, or Firm* — Keller Preece PLLC

(57) ABSTRACT

The present disclosure relates to systems, apparatuses, and methods for continuous cultivation and recovery of comestible non-human animal cells in a suspension bioreactor. For example, in one or more implementations, the disclosed methods include cultivating non-human animal cells in suspension culture within a bioreactor vessel, removing a measure of suspension culture from the bioreactor vessel while continuing to provide cell culture media thereto, and recovering a first portion of cultivated non-human animal cells from the removed measure of suspension culture while returning a second portion of cultivated non-human animal cells to the bioreactor vessel. Also, in some implementations, the disclosed systems include at least one sterile output module configured to prevent backflow contamination when recovering cultivated cells and removing spent media during continuous cultivation of non-human animal cells according to the disclosed methods.

20 Claims, 9 Drawing Sheets

500

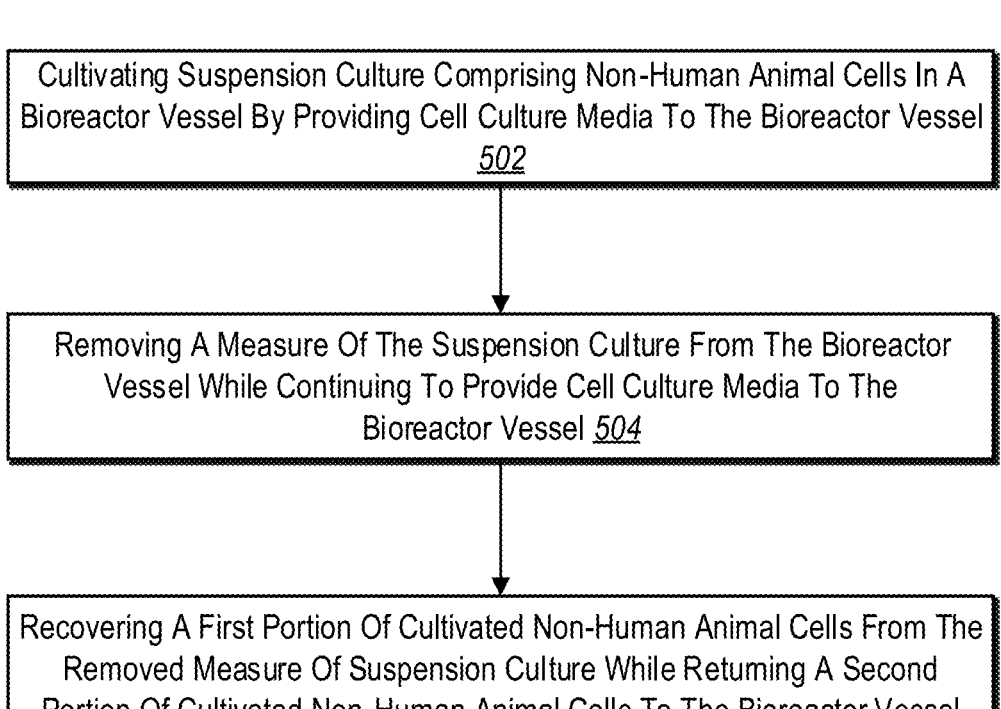

Cultivating Suspension Culture Comprising Non-Human Animal Cells In A Bioreactor Vessel By Providing Cell Culture Media To The Bioreactor Vessel
502

Removing A Measure Of The Suspension Culture From The Bioreactor Vessel While Continuing To Provide Cell Culture Media To The Bioreactor Vessel 504

Recovering A First Portion Of Cultivated Non-Human Animal Cells From The Removed Measure Of Suspension Culture While Returning A Second Portion Of Cultivated Non-Human Animal Cells To The Bioreactor Vessel
506

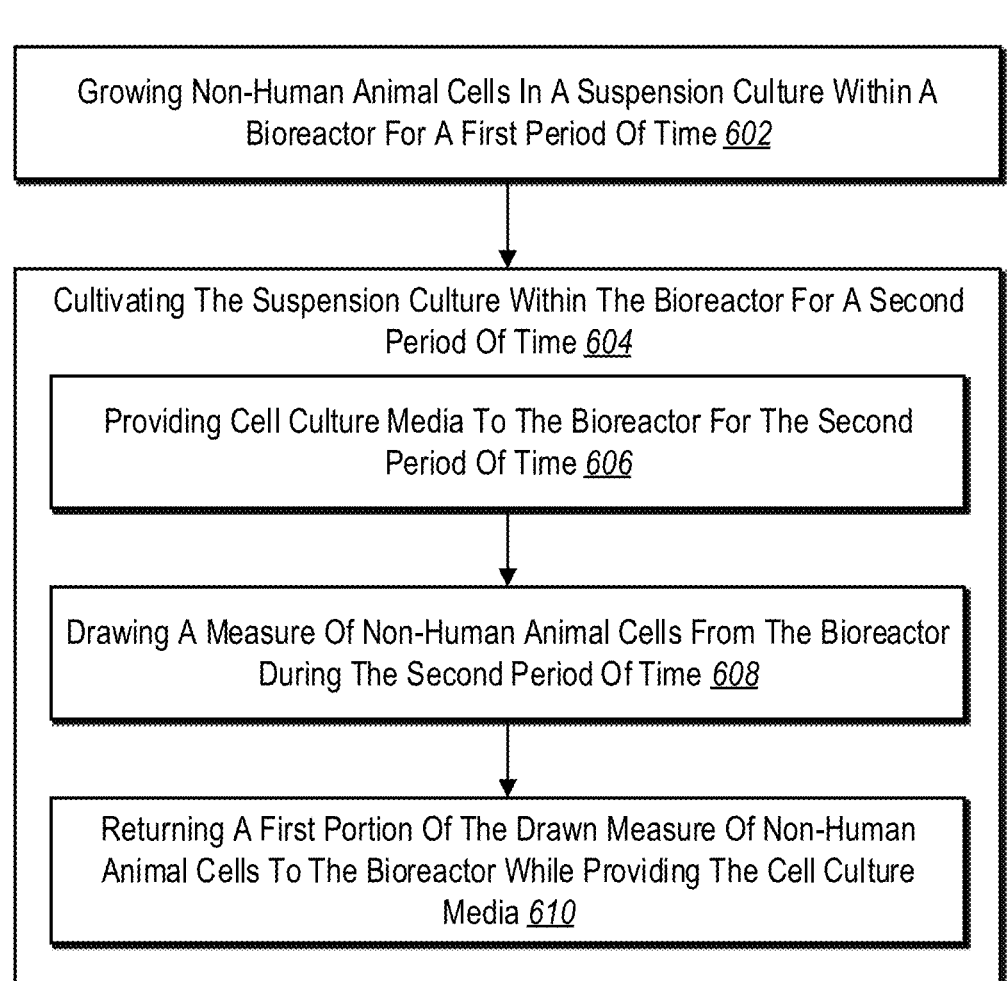

Growing Non-Human Animal Cells In A Suspension Culture Within A Bioreactor For A First Period Of Time *602*

Cultivating The Suspension Culture Within The Bioreactor For A Second Period Of Time *604*

Providing Cell Culture Media To The Bioreactor For The Second Period Of Time *606*

Drawing A Measure Of Non-Human Animal Cells From The Bioreactor During The Second Period Of Time *608*

Returning A First Portion Of The Drawn Measure Of Non-Human Animal Cells To The Bioreactor While Providing The Cell Culture Media *610*

*Fig. 6*

SYSTEMS AND METHODS FOR CONTINUOUS CULTIVATION AND RECOVERY OF COMESTIBLE NON-HUMAN ANIMAL CELLS

BACKGROUND

As the world's population continues to grow, cell-based or cultured animal products for consumption have emerged as an attractive alternative (or supplement) to conventional slaughtered animal products, such as meat from animals and supplemental products derived therefrom. For instance, cell-based, cultivated, or cultured meat represents a technology that could address the specific dietary needs of humans. Cell-based animal food products can be prepared from one or more of cultivated adherent and suspension cells derived from a non-human animal. Cell-based meat products, for instance, are often formed and shaped to mimic familiar forms of conventional meat.

In addition to addressing dietary needs, cell-based animal food products help alleviate several drawbacks linked to conventional animal products for humans, livestock, and the environment. For instance, conventional meat production involves controversial practices associated with animal husbandry, slaughter, and harvesting. Other drawbacks associated with harvested or slaughtered meat production include low conversion of caloric input to edible nutrients, microbial contamination of the product, emergence and propagation of veterinary and zoonotic diseases, relative natural resource requirements, and resultant industrial pollutants, such as greenhouse gas emissions and nitrogen waste streams.

Despite advances in creating cell-based animal food products, existing methods or systems for cultivating and processing cell-based animal food products face several shortcomings, such as challenges with capital utilization, cost, efficiency, and equipment maintenance. For example, existing methods for cultivating and processing cell-based animal food products often suffer from slow cellular growth, low yields of cell-based products, and an overall inefficient use of capital equipment. In particular, existing methods require prohibitive amounts of time and resources to generate small amounts of cell-based animal food products. To compensate for slow times of growing comestible mammalian or avian cells in suspension, for example, some manufacturers ramp up the same existing methods by increasing the number and size of machines and tools used to grow comestible non-human animal cells. However, such upscaling of cultivation equipment presents additional challenges with respect to overall equipment and supply costs, sterility and cleanability of bioreactors and support equipment, and harvest yield of cultivated cells. Relatedly, many conventional systems and methods, particularly when upscaled for increased production, are not able to produce meat at a higher rate, proportionately. These, along with additional problems and issues persist in existing methods for producing cell-based animal food products and derivatives thereof.

BRIEF SUMMARY

This disclosure generally describes systems, apparatuses, and methods for continuous cultivation and recovery of comestible non-human animal cells in a suspension bioreactor. For example, one or more embodiments include a bioreactor system that, when in an operation state, constantly recovers cells and constantly adds cell culture media to maintain a steady state condition. Furthermore, the bioreactor system removes spent cell culture media and replaces the spent cell culture media with fresh cell culture media. Additionally, the system also returns a portion of a concentrated cell stream to the suspension bioreactor, while simultaneously recovering another portion of the concentrated cell stream.

Specifically, in one or more implementations, the disclosed methods involve continuously cultivating non-human animal cells in a suspension bioreactor while partially recovering cultivated cells from removed suspension culture and returning a portion of concentrated cells from the removed suspension culture to the suspension bioreactor to maintain a steady state cell concentration for continued cultivation. Also, in some cases, the disclosed methods include separating at least a portion of culture broth from suspension culture removed or drawn from the bioreactor during partial recovery of cultivated cells and returning the separated culture broth to the suspension bioreactor for continued cultivation.

Additional features and advantages of one or more implementations of the present disclosure are outlined in the description which follows, and in part will be obvious from the description, or may be learned by the practice of such example implementations.

BRIEF DESCRIPTION OF THE DRAWINGS

Various implementations will be described and explained with additional specificity and detail through the use of the accompanying drawings, which are summarized below.

FIG. 5 a flowchart of a first series of acts for producing comestible non-human animal cells in accordance with one or more implementations of the present disclosure.

FIG. 6 illustrates a flowchart of a second series of acts for producing comestible non-human animal cells in accordance with one or more implementations of the present disclosure.

DETAILED DESCRIPTION

Figure 1:
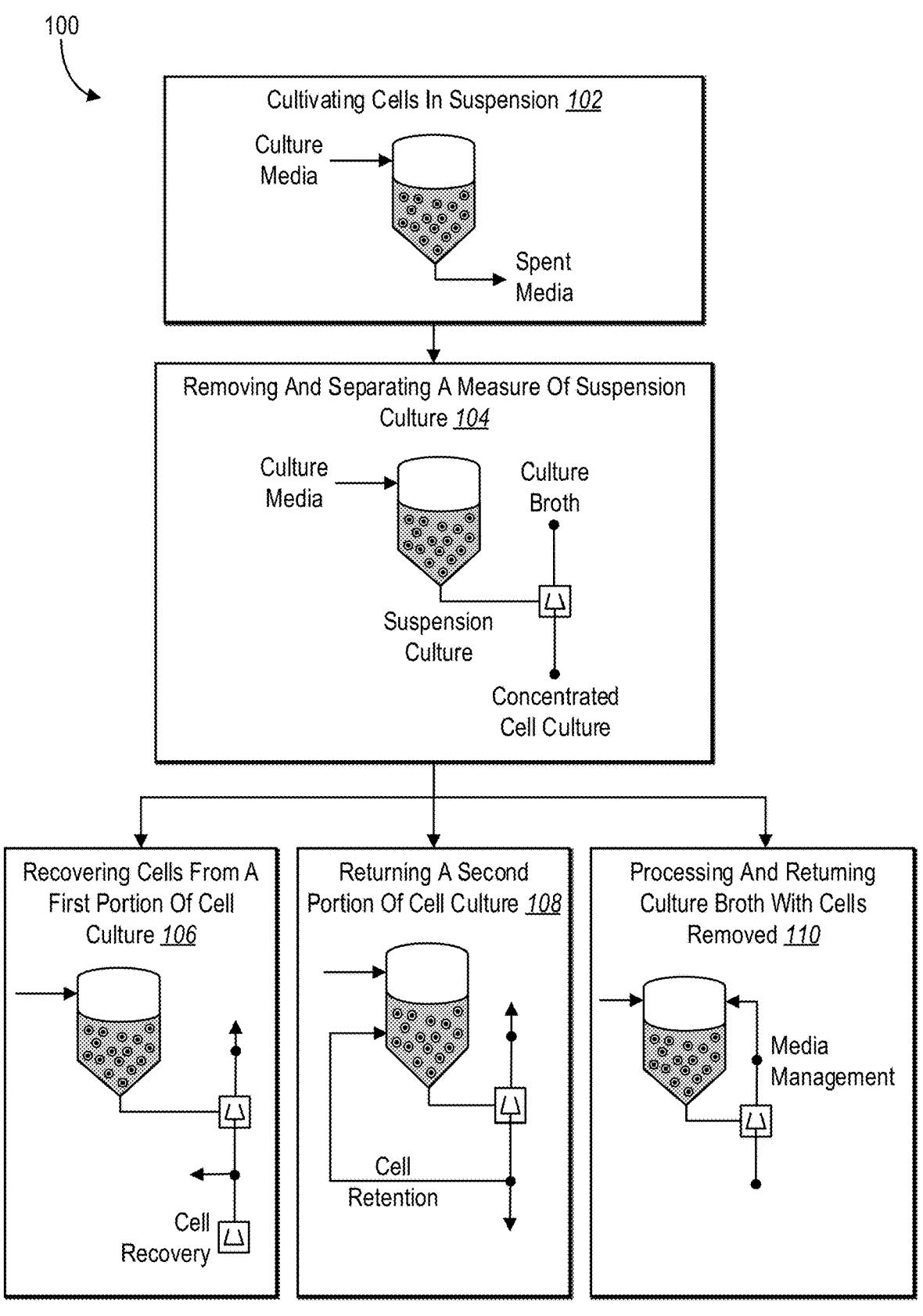
FIG. 1 illustrates an overview diagram of producing comestible non-human animal cells in accordance with one or more implementations of the present disclosure.

This disclosure describes implementations of systems, apparatuses, and methods for continuous cultivation and recovery of comestible non-human animal cells in a suspension culture. In one or more implementations, for example, the disclosed methods include continuously cultivating non-human animal cells in a suspension culture within a bioreactor while removing a measure of suspension culture from the bioreactor, recovering a portion of cultivated cells from the removed suspension culture, and returning a portion of the drawn suspension culture to the bioreactor to maintain a steady state cell concentration of cells for continued cultivation. Also, in some implementations, the disclosed methods include separating the drawn suspension culture into a concentrated cell culture and a culture broth with cells removed and returning at least a portion of the culture broth to the bioreactor for continued cultivation.

To illustrate, in some implementations, the disclosed methods include growing non-human animal cells in a suspension culture within a bioreactor for a first period of time and continuing to cultivate non-human animal cells within the suspension culture for a second period of time while partially recovering cultivated cells therefrom. For example, during the second period of time, the disclosed methods can include continuously providing cell culture media to the bioreactor, drawing a measure of cultivated cells from the bioreactor, and returning at least a first portion of the drawn measure of cultivated cells to the bioreactor while continuing to provide cell culture media thereto. Also, in some implementations, the disclosed methods include continuously returning the first portion of the drawn measure of cultivated cells to the bioreactor while recovering a second portion of the drawn measure of cultivated cells from the bioreactor system.

Further, in one or more implementations, the disclosed systems include one or more apparatuses for the continuous cultivation and recovery of comestible non-human animal cells within a suspension bioreactor system. In some implementations, for example, a bioreactor system for continuous cultivation of non-human animal cells includes at least one bioreactor vessel, a sterile retention device configured to separate suspension culture received from the bioreactor vessel into a concentrated cell culture and a culture broth with cells removed, a cell retention return configured to send a first portion of the concentrated cell culture back to the bioreactor vessel during continuous cultivation, and a cell recovery line for partially recovering cultivated cells from a second portion of the concentrated cell culture. Also, in some implementations, the suspension bioreactor system includes a cell concentration device configured to remove spent cell culture media from concentrated cell culture provided by the cell recovery line to recover cultivated cells.

In one or more of the disclosed implementations of the disclosed systems include at least one sterile output module configured to prevent backflow contamination within a suspension bioreactor system when recovering cultivated cells and removing spent media during continuous cultivation of cells. To illustrate, in some implementations, a sterile output module comprises at least two parallel output lines configured for alternating use and sterilization during flow of the second portion of the concentrated cell culture from the sterile cell retention device to the cell concentration device.

The disclosed methods provide several benefits relative to existing systems and methods for producing comestible cell-based animal food products. For example, existing suspension bioreactor systems and methods often require full batch production of cultivated cells prior to harvesting and require more volume of equipment to produce a given amount of cell mass per time. In contrast, the disclosed systems and methods optimize for pounds per year per volume of bioreactor by providing continuous recovery of cultivated cells while retaining portions of concentrated cells and culture broth for steady state cell growth with reduced levels of process stream discard. Accordingly, the disclosed methods increase process efficiency and decrease equipment costs over existing systems and methods for the production of cell-based animal food products. In one or more implementations, the disclosed systems and methods support high cell density cultures by continuously purging inhibitory by-products and providing fresh nutrients, enhancing productivity and product yield. Furthermore, the disclosed systems and methods are able to maintain a consistent cell growth rate and cell concentration by controlling the dilution rate (rate of media addition).

The disclosed systems and methods provide for increased sterility of bioreactor systems during the continuous cultivation and partial recovery of one or more embodiments. For example, in some implementations, the disclosed systems include one or more sterile output modules configured to prevent backflow contamination as materials are recovered (e.g., removed or recovered) from the corresponding bioreactor system. As described in greater detail below (e.g., in relation to FIGS. 2-3), the various features of the disclosed systems, apparatuses, and methods provide for increased sterility of suspension bioreactor systems.

As illustrated by the foregoing discussion, the present disclosure utilizes a variety of terms to describe features and advantages of the disclosed systems and methods. Additional detail is now provided regarding the meaning of such terms. As used herein, the term "cells" refers to cells that are useful for forming a cell-based food product for consumption. Generally, cells may comprise non-human mesenchymal progeny. For instance, cells may comprise at least one of muscle cells, muscle progenitor cells, or muscle support cells. In particular, cells may comprise different cell types, such as one or more of myoblasts, mesangioblasts, myofibroblasts, mesenchymal stem cells, embryonic stem cells, hepatocytes, fibroblasts, pericytes, adipocytes, epithelial, chondrocytes, osteoblasts, osteoclasts, pluripotent cells, somatic stem cells, endothelial cells, or other similar cell types. Furthermore, cells may comprise different types of progenitor cells, including myogenic progenitors, adipogenic progenitors, mesenchymal progenitors, or other types of progenitor cells. In some instances, the cells may comprise cells from distinct lineages, such as ectoderm or endoderm lineages, that have been transdifferentiated into cells useful for forming a cell-based food product for consumption, such as those cell types described above.

As used herein, the terms "cell-based food product" and "cell-based animal food product" refer to a food product comprising non-human animal cells grown in vitro. For instance, the cell-based food product can include isolated cells from animals combined with other ingredients or additives such as, but not limited to, plant proteins, salts, flavorings, acids. Such products are interchangeably referred to as in vitro meat product, in vitro food product, lab grown meat, cultured food, or slaughter-free meat, depending on context.

As used herein, the term "suspension culture" (or "cell culture") refers to cells growing in an at least partially liquid growth medium in which cells grow, multiply, and/or maintain nourishment. In particular, a suspension includes an agitated growth medium that is housed in a container in which single cells or small aggregates of cells grow, multiply, and/or maintain nourishment from the nutrients of the agitated growth medium. Cells grown in suspension are not attached to a substrate and therefore differ from a conventional adherent culture.

Also, as used herein, the terms "cell culture media" or "culture media" refer to a liquid or gel comprising compounds that support the growth of cells. In particular, cell culture media comprises sources of energy and compounds to regulate the cell cycle. For example, a cell culture media can contain amino acids, vitamins, inorganic salts, glucose, dissolved gases, serum, growth factors, hormones, and attachment factors. The cell media may also help maintain pH and osmolarity during cell growth and proliferation.

Also, as used herein, the term "culture broth" refers to a cell culture media from which cultivated cells have been removed (e.g., as described below in relation to FIGS. 1-2). Relatedly, as used herein, the term "spent cell culture media" or "spent media" refers to cell culture media that may include cell secreted products and that is at least partially depleted of nutrients during cultivation of cells, e.g. nutrients used by the cells. Accordingly, spent cell culture media is generally removed (e.g., extracted by filtration, centrifugation, and/or other processes) and replaced with new and/or reprocessed cell culture media during cultivation of cells within a bioreactor system.

As used herein, the term "bioreactor" (or "cultivator") refers to an apparatus in which cells are introduced, cultivated, and grown to form comestible meat cells of a cell-based food product. Bioreactors or cultivators are often part of a closed system for producing cells in a sterile environment. For example, a bioreactor system can comprise a sterile environment (e.g., devoid of foreign contaminants therein and separated/sealed from potential contaminants outside of a system boundary) having one or more bioreactor vessels (sometimes referred to as "suspension bioreactors") in fluidic communication with various sterile material supplies and sterile support equipment, such as described below in relation to FIGS. 2-3.

As used herein, the terms "sterile environment," "closed environment," and "closed bioreactor system," refer to a space with regulated environmental factors and physical boundaries. In particular, a closed environment or system includes a space in which certain parameters, such as pressure, temperature, segregation, and exposure to outside elements, are controlled. More specifically, external contaminants are limited, or nonexistent, within a closed environment or system. For instance, a closed environment or system is isolated from contaminants found in air (e.g., ambient air). Further, a closed environment or system comprises an area that is contained on all sides. In particular, a closed bioreactor system comprises an enclosed environment including one or more fluidly connected spaces that are at least substantially closed off from external contaminants. In another example, a closed environment or system comprises a transfer mechanism, such as a series of sterile containers including a cultivator and a harvest collector. The series of containers may be sterilized and sealed prior to receiving cells. In another example, a closed environment or system comprises a series of pipes for transporting and processing cells. In yet another example, a closed environment or system includes means for preventing backflow contamination from an external environment, such as when removing material from within the boundaries of the closed environment or system (e.g., as described below in relation to FIG. 3).

As used herein, the terms "drawn" or "drawing" refer to removal from a system or component of the system for processing. For example, suspension culture is drawn out of the bioreactor in one or more embodiments and subjected to moisture reduction (e.g., cell concentration). Drawn suspension culture can be returned to the bioreactor or permanently removed from the system via recovery.

As used herein, the terms "harvest" or "harvesting" refer to a process of removing cells from a closed environment, such as a closed bioreactor system. For example, in some cases, harvesting refers to the process of removing cells from a closed environment and exposing them to external air, such as the ambient air of a harvest room. Harvesting may comprise removing suspension cells from a closed environment. In one or more implementations, harvesting comprises opening a harvest collector holding cells, wherein the cells are exposed to air (e.g., ambient air, filtered air, and/or refrigerated air) and any contaminants therein.

As used herein, the terms "recovery" or "recovering" refer to a process where cells are removed from a growth environment of a given bioreactor. For example, cells are "recovered" from a bioreactor if they are not later returned to that same bioreactor. Recovered cells may be transferred to a new growth environment or the recovered cells may be transferred in a terminal manner, such as for harvesting. Further, recover may comprise removal of cells from a bioreactor system without necessarily exposing the recovered cells to air (e.g., removing the cells from the bioreactor system directly to a sealed container). In some implementations, recovery also comprises separating cells from a cell culture media (e.g., a spent growth or nutrient media).

Additional detail will now be provided regarding the disclosed systems, apparatuses, and methods in relation to illustrative figures portraying example implementations. FIG. 1 illustrates an example process for preparing comestible non-human animal cells in accordance with one or more implementations. By way of overview, FIG. 1 illustrates a series of acts 100 comprising an act 102 of cultivating non-human animal cells (e.g., mammalian or avian or fish cells) within a suspension bioreactor, an act 104 of removing (e.g., drawing) a measure of suspension culture from the suspension bioreactor and separating the measure of suspension culture into a concentrated cell culture and a culture broth with cells removed, an act 106 of recovering cultivated cells from a first portion of the concentrated cell culture, an act 108 of returning a second portion of the concentrated cell culture to the suspension bioreactor for continued cultivation, and an act 110 of processing and returning culture broth, or a fraction thereof, to the suspension bioreactor. FIGS. 2-6 and the corresponding paragraphs herein provide further detail with regard to continuous cultivation and recovery of comestible non-human animal cells in accordance with one or more implementations.

As shown in FIG. 1, in one or more implementations, non-human animal cells are grown within a suspension bioreactor by performing the act 102 of cultivating the non-human animal cells by providing (e.g., delivering) a cell culture media to the suspension bioreactor. In some implementations, for example, the act 102 comprises introducing cell culture media into a bioreactor vessel having a suspension culture of non-human animal cells disposed therein. As also shown, spent cell culture media (e.g., media that is partially or completely depleted of nutrients) is removed from the bioreactor vessel as additional cell culture media (e.g., fresh nutritive media) is introduced thereto. In some implementations, for example, spent cell culture media is removed by one or more methods including gravity settling, filtration, centrifugation, or other methods for removing spent media while retaining cells within the bioreactor vessel.

Accordingly, in one or more implementations, non-human animal cells are cultivated by providing cell culture media to a bioreactor vessel comprising (e.g., containing) suspension culture for a first period of time (e.g., for an initial cultivation period). In some implementations, for example, cells are cultivated within the bioreactor vessel until a target cell density (e.g., a packed cell volume (PCV) or a viable cell density (VCD)) is achieved within the bioreactor vessel. For instance, in one or more implementations, the first period of time comprises a predetermined period of time for initial cultivation, such as but not limited to 12 hours, 24 hours, 2 days, 5 days, 10 days, and so forth. Alternatively or additionally, the initial cultivation of cells within the bioreactor vessel can be performed until the target cell density is measured or estimated within the bioreactor vessel. In some implementations, for example, a sample is extracted from the bioreactor vessel and a PCV (or VCD) is determined from the extracted sample.

As also shown in FIG. 1, in one or more implementations, partial recovery of cultivated cells from the bioreactor system is initiated during a secondary cultivation period by performing the act 104 of drawing a measure of suspension culture from the suspension bioreactor and separating the measure of suspension culture into a concentrated cell culture and a culture broth with cells removed. In some implementations, for example, a sterile cell retention device (e.g., as described below in relation to FIG. 2) receives suspension culture drawn from the bioreactor vessel and separates the drawn suspension culture into the concentrated cell culture (e.g., a heavy phase) and the culture broth with cells removed (e.g., a light phase).

In some implementations, having separated the drawn measure of suspension culture into a concentrated cell culture and a culture broth with cells removed, partial cell recovery is performed in a cell recovery act 106. In one or more implementations, for example, a first portion of the concentrated cell culture is recovered from the sterile environment of the depicted suspension bioreactor system and further processed to produce a comestible cell-based food product. In some implementations, for instance, the recovered non-human animal cells are further concentrated a second time utilizing a cell concentration device (e.g., as described below in relation to FIG. 2) to remove spent media from the first portion of concentrated cell culture.

In one or more implementations, a second portion of the concentrated cell culture separated from the drawn suspension culture is retained for further cultivation by performing a cell retention act 108 of returning the second portion of the concentrated cell culture to the suspension bioreactor. In some implementations, for example, a steady state cell density (e.g., a packed cell volume within a target range) is maintained within the suspension bioreactor at least in part by returning the second portion of concentrated cell culture to the bioreactor vessel for continued cultivation of non-human animal cells therein. Accordingly, in certain implementations, cultivated cells are continuously recovered from suspension culture drawn from the suspension bioreactor while a portion of the concentrated cell culture are returned to the suspension culture for continued cultivation of cells within the bioreactor vessel.

Additionally, in some implementations, at least a portion of cell culture media drawn from the suspension culture (e.g., at the act 104) is retained by performing a media management act 110 of processing and returning culture broth to the suspension bioreactor. In one or more implementations, for example, the culture broth separated from the suspension culture is conditioned, stripped of gases, sparged with bubbles, air-lifted, and/or amended with shear protectant (e.g., by introducing pluronics or other additives). In one or more implementations, with the cells separated from the culture broth, a variety of media management procedures are performed in preparation of reintroducing the culture broth to the bioreactor vessel for continued cultivation of non-human animal cells that would not be possible in the presence of cells, e.g., would damage the cells.

As mentioned previously, the disclosed implementations can also include systems and apparatuses for the continuous cultivation and recovery of comestible non-human animal cells within a suspension bioreactor system. For example, FIG. 2 illustrates a suspension bioreactor system 200 comprised of various components configured for continuous cultivation and recovery of cells within a sterile environment.

Figure 2:
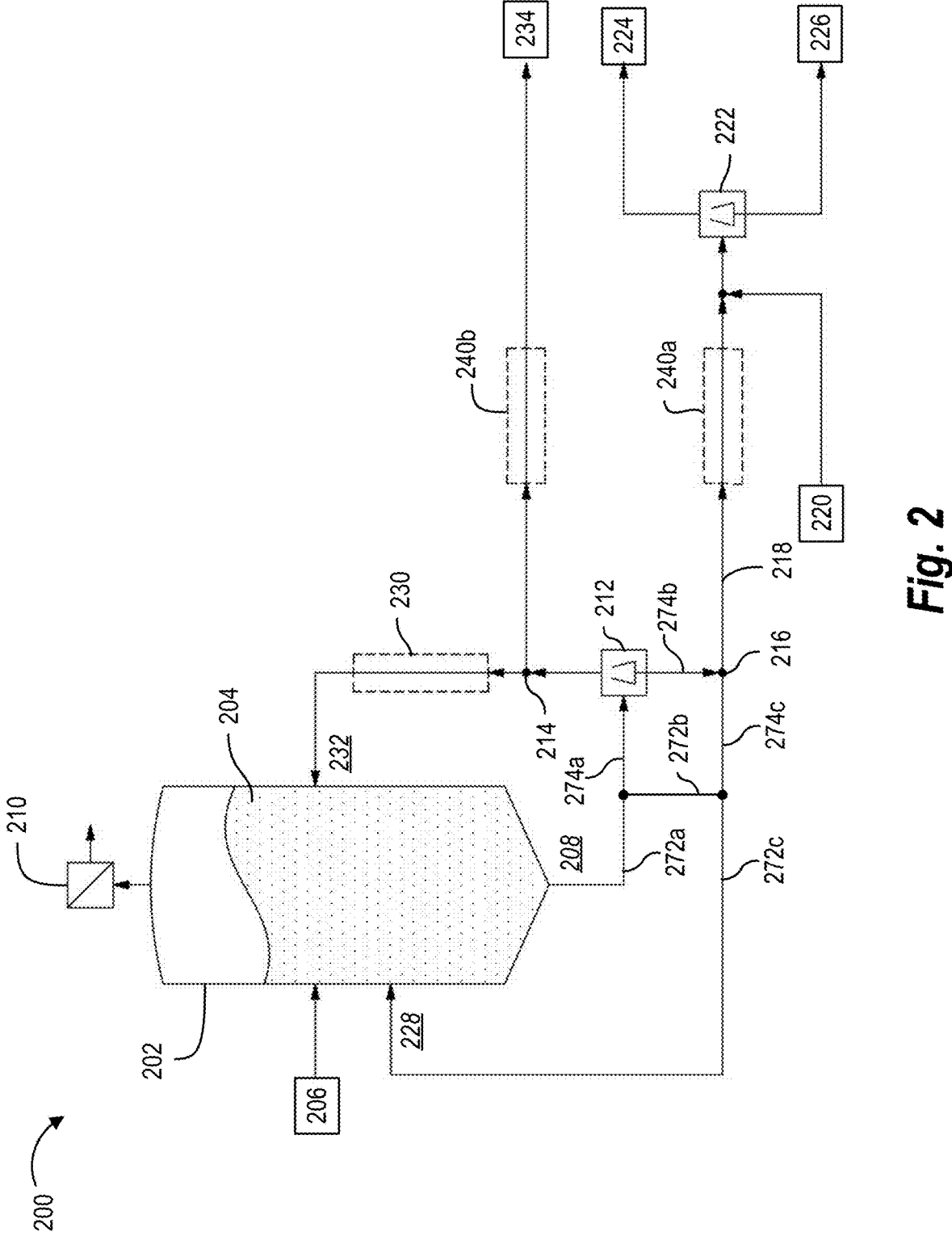
FIG. 2 illustrates a suspension bioreactor system for continuous cultivation and recovery of comestible non-human animal cells in accordance with one or more implementations of the present disclosure.

As shown in FIG. 2, for instance, the suspension bioreactor system 200 comprises a bioreactor vessel 202 configured to cultivate a suspension culture 204 comprising non-human animal cells (e.g., for use in the production of a comestible cell-based food product). In some implementations, for example, the bioreactor vessel 202 comprises a suspension bioreactor with a 10,000 liter capacity. In other implementations, the bioreactor vessel 202 comprises a capacity less or more than 10,000 liters, such as a capacity between 500 liters, 1000, liters, 2000 liters, 5000 liters, 15,000 liters, 20,000 liters, 50,000 liters, 75,000 liters, 100,000 liters, 250,000 liters, etc. As illustrated, the bioreactor vessel 202 is loaded with non-human animal cells and a cell culture media is delivered to the bioreactor vessel 202 (e.g., from a cell culture media stream 206) to cultivate the non-human animal cells therein. As mentioned above, in one or more implementations, cells are initially cultivated within the bioreactor vessel 202 for a first period of time (e.g., until a particular cell density within the suspension culture 204 is achieved such as 5% PVC, 10% PVC, 15% PVC) in preparation for continuous cultivation and partial recovery of cells from the bioreactor vessel 202 during a second period of time, according to the methods disclosed herein (e.g., as further described in relation to FIGS. 1 and 4-6).

As further illustrated in FIG. 2, the suspension bioreactor system 200 in cell culture media stream 206 configured to introduce cell culture media (e.g., fresh nutritive media) into the bioreactor vessel 202 to replenish any spent media removed from the bioreactor vessel 202. During initial cultivation, for instance, spent media is removed from the bioreactor vessel 202 while retaining cells within the suspension vessel 202 for continued cultivation via nutrients provided by the cell culture media stream 206. In one or more implementations, cell culture media is flowed into the bioreactor vessel 202 at a gradually increasing flow rate during initial cultivation until a steady state cultivation flow rate, which is maintained during continuous cultivation and partial recovery of cultivated cells. In one or more implementations, for example, the steady state cultivation flow rate comprises about 5 vessel volumes per day (VVD). In other implementations, the steady state cultivation flow rate comprises between 1 VVD and 20 VVD (e.g., 2 VVD, 7 VVD, 10 VVD, 15 VVD, etc.), depending at least in part on the growth rate of cells within the suspension bioreactor.

In certain implementations, a measure of the suspension culture 204, including cultivated cells, is drawn from the bioreactor vessel 202 via a suspension culture line 208 for partial recovery and partial cell retention, as suspension culture within the bioreactor vessel 202 is continuously cultivated (e.g., for the aforementioned second period of time). In some implementations, for example, the suspension culture line 208 draws a stream of suspension culture at a rate of about 14 VVD for partial cell recovery and partial cell retention. In other implementations, the suspension culture line 208 draws a stream of suspension culture at an extraction flow rate between 5 VVD and 20 VVD, depending at least in part on cell growth rates within the bioreactor vessel, cell retention rates, and/or cell recovery rates.

As also shown, the suspension bioreactor system 200 includes a sterile cell retention device 212 configured to separate the measure of the suspension culture 204 from the suspension culture line 208 into a concentrated cell culture (e.g., a heavy phase of 3X cell density compared to the provided suspension culture 204) and a culture broth with cells removed (e.g., a light phase with a negligible or relatively small density of cultivated cells). In some implementations, for example, the sterile cell retention device 212 separates the suspension cell culture stream into one part concentrated cell culture and two parts culture broth with cells removed. The sterile cell retention device 212 can include, for example, a continuous flow centrifuge configured to separate received materials within a sterile environment (e.g., a centrifuge comprising sealed components and/ or other features for maintaining sterility within a closed system). Alternative examples of sterile cell retention devices include, but are not limited to, apparatuses configured for sterile filtration, gravity sedimentation, magnetic separation, and so forth.

As illustrated, the suspension bioreactor system 200 further comprises a cell recovery line 218 for recovering cultivated cells from at least a portion of the measure of the suspension culture 204 drawn from the bioreactor vessel 202. In particular, the cell recovery line 218 is configured to receive a first portion of the concentrated cell culture provided by the sterile cell retention device 212 for recovery from the suspension bioreactor system 200. As shown, for example, the suspension bioreactor system 200 also includes a wash buffer line 220 configured to deliver wash buffer to dilute and/or wash the portion of the concentrated cell culture received via the cell recovery line 218 prior to secondary processing via a cell concentration device 222. In some implementations, for example, the wash buffer line 220 introduces one part wash buffer to one part concentrated cell culture received from the sterile cell retention device 212. To recover cultivated cells from the concentrated cell culture, the cell concentration device 222 separates the concentrated cell culture received via the cell recovery line 218 into spent media 224 (e.g., wash buffer and/or cell culture media that is at least partially depleted of nutrients) and recovered cells 226 (e.g., a heavy phase wet mass comprising further concentrated cell culture). In some embodiments, for example, the cell concentration device 222 further concentrates the cell culture by a factor between 3× and 5× to produce a mass of recovered cells 226 comprising about 70% cells per volume (e.g., packed cell volume).

Furthermore, as shown in FIG. 2, the suspension bioreactor system 200 comprises a cell retention line 228 configured to return at least a portion of the concentrated cell culture output by the sterile cell retention device 212 to the bioreactor vessel 202 for continued cultivation. In some implementations, for example, a first portion of the concentrated cell culture is continuously recovered (e.g., removed from the suspension bioreactor system 200) while a second portion of the concentrated cell culture is returned to the bioreactor vessel 202 in order to maintain a particular or desired cell density in the suspension culture 204 within the bioreactor vessel 202 during cultivation (e.g., as further described below in relation to FIG. 4). Specifically, a valve or stream divider 216 can be controlled to split the concentrated cell culture to send a first portion to cell recovery via the cell recovery line 218 and a second portion back to the bioreactor vessel 202 via the cell retention line 228. In some embodiments, the cell retention line 228 is in fluid communication with a reservoir comprising cell retentate conditioning materials that may be introduced (e.g., injected) into the cell retention line 228, where the conditioning materials refresh or otherwise revitalize the cell retentate before returning to the bioreactor.

In one or more implementations, the cell retention line 228 enables the maintenance of a higher cell density by mitigating waste component build up, e.g., ammonia and lactate, mitigating spent media accumulation, and helping ensure a constant supply of fresh nutrients, e.g., growth factors and amino acids that have short half-lives. One will appreciate that this would not occur in a simple chemostat style reactor lacking a return of concentrated cells. In some implementations, for example, the suspension bioreactor system 200 recovers between 2.5% to 50% of the concentrated cell culture via the cell recovery line 218, while the returning 50% to 97.5% of the concentrated cell culture back into the bioreactor vessel 202. Furthermore, in some implementations, the suspension bioreactor system 200 recovers between 5% to 25% of the concentrated cell culture via the cell recovery line 218, while the returning 75% to 95% of the concentrated cell culture back into the bioreactor vessel 202. Still further, in some implementations, the suspension bioreactor system 200 recovers between 5% to 15% of the concentrated cell culture via the cell recovery line 218, while the returning 85% to 95% of the concentrated cell culture back into the bioreactor vessel 202. In some implementations, the suspension bioreactor system 200 recovers between 5% to 10% of the concentrated cell culture via the cell recovery line 218, while the returning 90% to 95% of the concentrated cell culture back into the bioreactor vessel 202.

In some implementations, it is advantageous to position the cell retention device 212 a particular distance from the bioreactor vessel 202 (e.g., separated by a relatively large distance), to allow for the cell retention device 212, or one or more cell retention devices, to be used with multiple reactors, and to reduce certain design constraints (e.g., allowing flexibility in floor plans and equipment layouts). However, a retention time of the cells passing through the cell retention device 212 and back to the bioreactor vessel 202 should be a short enough time length such that the cells do not succumb to hypoxia, pH shifts, excessive $CO_2$ accumulation, temperature fluctuation, or experience other related negative effects, while separated from the bioreactor vessel 202, which is continually oxygenated, to ensure the cells' continued ability to proliferate after returning to the bioreactor vessel 202.

To accommodate the dual needs of a short retention time and a relatively distant concentration device, for example, the bioreactor system 200 may include a bypass line 272b. The bypass line 272b enables a decoupling of distance, concentration device flow rate, and residence time by separating the suspension culture line 208 into two separate zones, a first zone 272a-c, having a higher flow rate, and a second zone 274a-c, having a lower flow rate. In one non-limiting example, the first zone 272a-c operates at a flow rate of 10 L/min at section 272a, 8 L/min at section 272b (e.g., within the bypass line 272b), and 9 L/min at section 272c, while the second zone 274a-c operates at a flow rate of 2 L/min, e.g. across sections 274a-c. The second zone 274a-c operates at a flow rate conducive to an optimal operation of the cell retention device 212 and the length of the second zone is tailored to reduce residence time. In contrast, the first zone 272a-c operates at a high flow rate, e.g., as high as the cells can withstand without being damaged by shear, to enable a greater distance between the bioreactor vessel 202 and the cell retention device 212, while keeping cell residence times within tolerance, e.g., 1 min. In this manner, the bypass line 272b balances the competing needs of a short residence time and a distant cell retention device 212 requiring particular flow rates. In one embodiment, the first zone 272a-c and the second zone 274*a-c* are temperature controlled. In one example, a length of the first zone 272*a-c* is longer than a length of the second zone 274*a-c*. In other examples, a ratio of the first zone 272*a-c* length to the second zone 274*a-c* length is between 100:1 and 3:1.

As also shown in FIG. 2, the suspension bioreactor system 200 includes a culture broth retention line 232 configured to return at least a portion of the culture broth with cells removed to the bioreactor vessel 202 for further cultivation of cells therein. As illustrated, in certain implementations the culture broth retention line 232 includes a media management module 230 configured to process (e.g., condition) the culture broth for reintroduction into the bioreactor vessel 202. To illustrate, media processing performed by the media management module 230 can include, but is not limited to, gas stripping, small bubble sparge, air lifting, media conditioning, or introduction of shear protectants (e.g., using pluronics). Further, in one or more implementations, at least a portion of the culture broth with cells removed, comprising spent media 234, is discarded or otherwise removed from the suspension bioreactor system 200. In some implementations, for example, about one part of the culture broth with cells removed is removed as spent media 234, while one part of the culture broth is reintroduced into the bioreactor vessel 202. Specifically, a valve or stream divider 214 can be controlled to split the culture broth with cells removed to send a first portion to be removed as spent media 234 and a second portion back to the bioreactor vessel 202 via the culture broth retention line 232.

As also shown in FIG. 2, the suspension bioreactor system 200 includes various elements for maintaining a sterile environment during the foregoing procedures by reducing and/or preventing contamination from entering the suspension bioreactor system 200. As illustrated, for instance, the bioreactor vessel 202 comprises a sterile vent filter 210 configured to allow excess vapors and/or gases to exit the bioreactor vessel 202 while restricting contamination from elements outside of the bioreactor vessel 202. In one or more implementations, as illustrated, the suspension bioreactor system 200 includes one or more sterile output modules 240*a*, 240*b*, each configured to prevent backflow contamination as materials are extracted from the bioreactor system 200. Specifically, the sterile output module 240*a* is configured to prevent backflow contamination from entering the sterile environment of the suspension bioreactor system 200 during continual drawing of cells from the concentrated cell culture during cell recovery (e.g., by preventing backflow contamination between the cell concentration device 222 and at least one of the cell retention stream or the sterile cell retention device). Similarly, the sterile output module 240*b* is configured to prevent backflow contamination from entering the suspension bioreactor system 200 as the spent media 234 is removed from the sterile environment of the suspension bioreactor system 200. In one or more implementations, the sterile output modules described herein (e.g., in relation to FIG. 3 below) can be implemented to provide boundaries between sterile and non-sterile components of the suspension bioreactor system.

Figure 3:
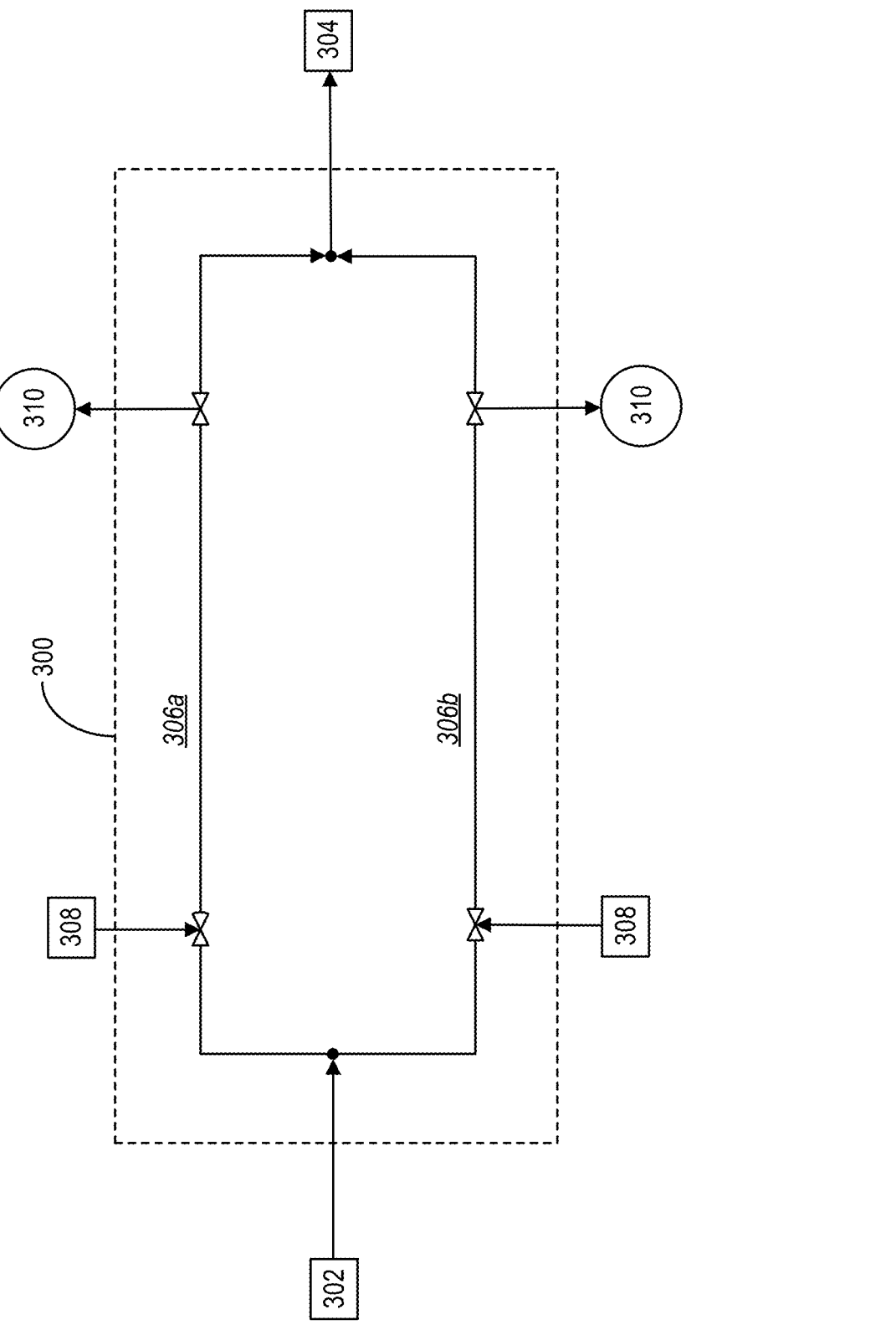
FIG. 3 illustrates a sterile output module of a bioreactor system in accordance with one or more implementations of the present disclosure.

To further illustrate, FIG. 3 shows a sterile output module 300 according to one or more implementations. As shown, the sterile output module 300 comprises an inlet line 302 configured to receive materials from a sterile environment, such as a bioreactor system, and an outlet line 304 configured to expend received materials therefrom. In particular, the sterile output module 300 is configured to provide a boundary between the sterile environment preceding the inlet line 302 and a non-sterile environment following the outlet line 304.

As also shown in FIG. 3, the sterile output module 300 comprises at least two parallel output lines 306*a*, 306*b* configured for alternating use and sterilization during flow of materials through the sterile output module 300. In other words, one of the parallel output lines 306*a*, 306*b* can be sealed off from the corresponding sterile system to be sterilized while the other is opened to allow materials from the inlet line 302 to flow through the outlet line 304. To illustrate, in one such implementation, the first output line 306*a* is opened and actively utilized as an output of the corresponding sterile system, while the second output line 306*b* is sealed from the system for sterilization. After a time period of the first output line 306*a* being open, contamination may begin to migrate upstream against the direction of flow, and first output line 306*a* is closed for sterilization of any such contamination while previously sterilized second output line 306*b* is opened to enable continuous use. In this manner, flow and sterilization alternate between the two lines and enable continuous flow. In the implementation shown, each of the parallel output lines 306*a*, 306*b* is equipped with a steam source 308 configured to receive steam and/or other sterilant into the respective line and a steam trap 310 configured to drain the steam and/or sterilant from the respective line. Accordingly, each of the parallel output lines 306*a*, 306*b* can be sterilized in place without disrupting use of the other by manipulating a series of valves.

As mentioned previously, in one or more implementations, the disclosed methods include (i) an initial cultivation of non-human animal cells within a suspension bioreactor until a target cell culture density is reached, (ii) a steady state cultivation of non-human animal cells comprising continuous cultivation and partial recovering of cultivated cells, and (iii) a final recovering of cultivated cells from the suspension bioreactor. To further illustrate, FIGS. 4A-4C provides example process graphs for producing comestible non-human animal cells within a suspension bioreactor having a capacity of 10,000 liters, in accordance with one or more implementations.

Figures 4A, 4B, 4C:
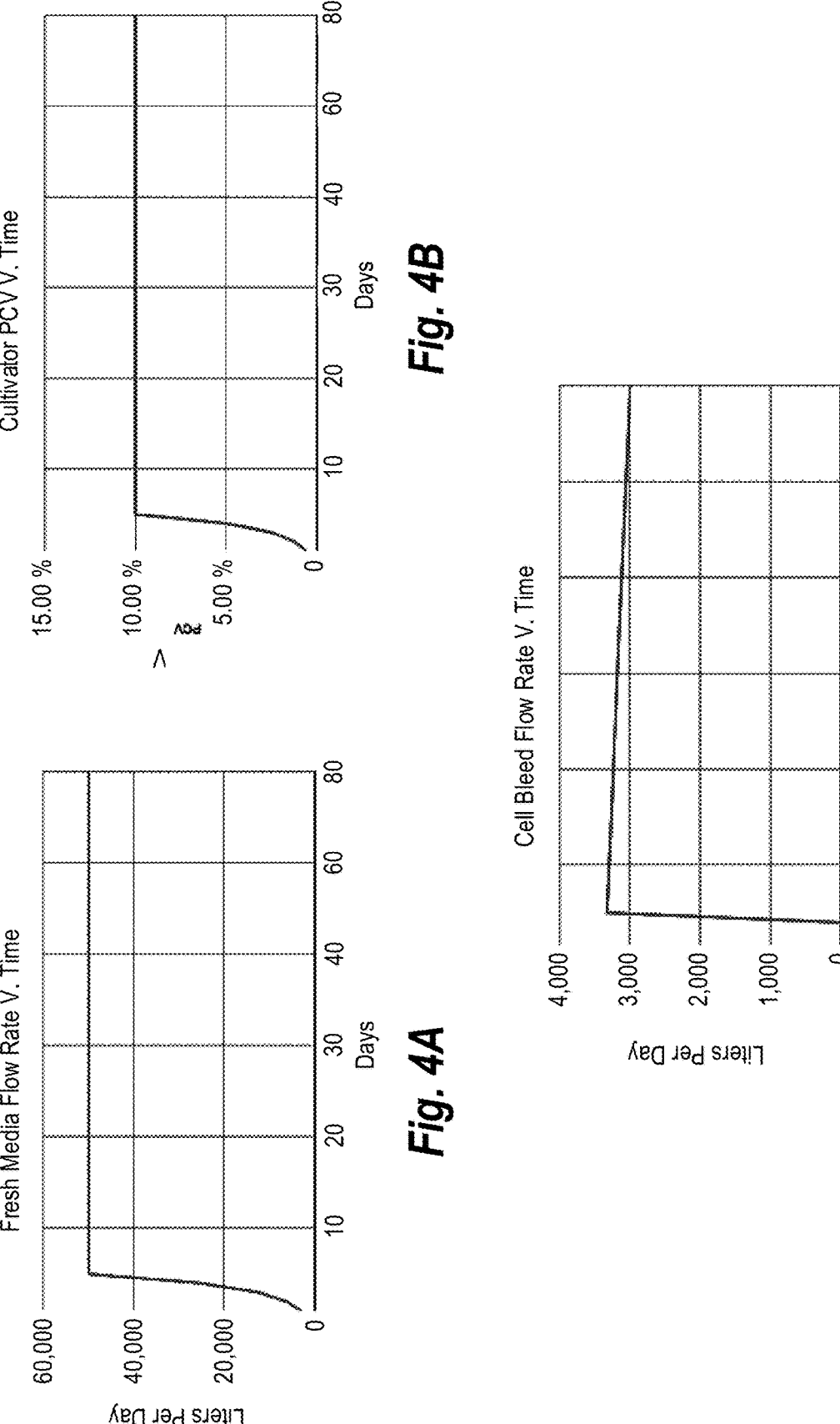
FIG. 4A-4C illustrate a series of process graphs for producing comestible non-human animal cells in accordance with one or more implementations of the present disclosure.

As shown in FIG. 4A, for instance, non-human animal cells are cultivated within a suspension bioreactor for a first period of time (e.g., an initial cultivation period) by filling the suspension bioreactor with cell culture media at a gradually increasing rate (indicated as "Fresh Media Flow Rate V. Time"). In the implementation shown, for example, the flow of cell culture media into the suspension bioreactor is gradually increased from about 3,150 liters per day at a beginning of an initial cultivation period to about 50,000 liters per day at a conclusion of the initial cultivation period.

Relatedly, as shown in FIG. 4B, a packed cell volume (PCV) (e.g., a cell density within the suspension bioreactor, indicated as "Cultivator PCV V. Time") gradually increases from an initial inoculation PCV of about 0.63% at the beginning of the initial cultivation to a target PCV of about 10.0% at the conclusion of the initial cultivation period. Moreover, as also shown in FIG. 4C, cultivated cells are not recovered from the suspension bioreactor (indicated as "Cell Bleed Flow Rate V. Time") during the initial cultivation period, e.g., 5 days.

While FIGS. 4A-4C illustrates a specific example of an initial cultivation period, implementations of the disclosed methods can include alternative lengths of time needed to reach a target cell density (e.g., PCV) within the suspension bioreactor. Furthermore, the values illustrated in FIGS.

4A-4C are for illustrative purposes-implementations can include various values depending on cultivation targets, system parameters (e.g., total bioreactor capacity and/or predetermined target cell densities), variations in cultivation yield rates, and so forth.

As also shown in FIG. 4C, non-human animal cells are continuously cultivated during a second period of time (e.g., a steady state cultivation period) by providing cell culture media in the suspension bioreactor at a constant (or nearly constant) rate while partially recovering cultivated cells from the suspension bioreactor. In the implementation shown, for example, cell culture media is provided at a predetermined steady state cultivation rate of about 50,000 liters per day and the cell density (e.g., PCV) within the suspension bioreactor is maintained at or near about 10.00% throughout the steady state cultivation period (e.g., about 55 days).

To maintain the target cell density within the suspension bioreactor during the steady state cultivation period, a first portion of cultivated cells separated from suspension culture drawn from the suspension bioreactor is recovered from the bioreactor system (indicated in FIG. 4C) while a second portion of the cultivated cells is returned to the suspension bioreactor for continued cultivation (e.g., as described above in relation to FIGS. 1-2). Furthermore, as shown in FIG. 4C, the rate at which cultivated cells are recovered is gradually decreased from an initial recovery stream flow rate of about 3,333 liters per day to about 3,000 liters per day (e.g., over 55 days of steady state cultivation). In other words, cultivated cells are returned to the suspension bioreactor at a gradually increasing or decreasing retention flow rate to match any variabilities in the cell growth rate within the suspension bioreactor, in order to maintain the target cell density within the suspension bioreactor. As further mentioned, in some implementations, at least a portion of culture broth with cells removed is also returned to the suspension bioreactor during steady state cultivation to sustain continuous cell growth while maintaining a constant flow rate of cell culture media into the suspension bioreactor.

To further illustrate, in the illustrated exemplary implementation, while providing cell culture media at a constant flow rate of about 50,000 liters per day, suspension culture is removed from the suspension bioreactor at a rate of about 140,000 liters per day. Using a sterile cell retention device (e.g., the sterile cell retention device 212), the suspension culture stream is separated into a concentrated cell culture (e.g., heavy phase) at about 46,667 liters per day and a culture broth with cell removed (e.g., light phase) at about 93,333 liters per day. Accordingly, as described above, in the foregoing example, a first portion of the culture broth with cells removed is processed and returned to the suspension bioreactor (e.g., at a rate of about 46,667 liters per day), while a second portion of the culture broth comprising spent media is discarded or otherwise removed from the bioreactor system (e.g., at a rate of about 46,667 liters per day).

In one or more implementations, a first portion of the concentrated cell culture is recovered from the bioreactor system (e.g., at an initial rate of about 3,333 liters per day) and a second portion of the concentrated cell culture is returned to the suspension bioreactor for continued cultivation (e.g., at an initial rate of about 43,333 liters per day). Also, as discussed above, the first portion of the concentrated cell culture can be recovered using a cell concentration device (e.g., the cell concentration device 222) to separate spent media therefrom to produce a further concentrated cell culture (e.g., a heavy phase wet mass). Additionally, an inline dilution using a wash buffer can be introduced to the first portion of concentrated cell culture (e.g., at a rate of 3,333 liters per day) during recovery to assist in removing spent media therefrom. Accordingly, in the foregoing example, further concentrated cell culture is recovered at an initial rate of about 1,429 liters per day, whereas spent media removed therefrom is discarded (or otherwise removed from the bioreactor system) at a rate of about 5,238 liters per day. As mentioned above, in one or more implementations, at a completion of the steady state cultivation phase, the suspension culture is removed from the suspension bioreactor and the cultivated cells remaining therein are recovered in a final recovery phase.

FIGS. 1-4C, the corresponding text, and the examples provide several different systems, methods, techniques, components, and/or devices relating to continuous cultivation and recovery of comestible non-human animal cells in suspension in accordance with one or more implementations. In addition to the above description, one or more implementations can also be described in terms of flow-charts including acts for accomplishing a particular result. FIGS. 5-6, for example, illustrate two such flowcharts of acts. The acts described herein may be repeated or performed in parallel with one another or in parallel with different instances of the same or similar acts.

As shown in FIG. 5, a series of acts 500 includes an act 502 of cultivating suspension culture comprising non-human animal cells in a bioreactor vessel by providing cell culture media to the bioreactor vessel, an act 504 of removing a measure of the suspension culture from the bioreactor vessel while continuing to provide cell culture media to the bioreactor vessel, and an act 506 of recovering a first portion of cultivated non-human animal cells from the removed measure of suspension culture while returning a second portion of cultivated non-human animal cells to the bioreactor vessel.

In some implementations, the series of acts 500 further comprises initially cultivating the suspension culture by providing the cell culture media to the bioreactor vessel for a first period of time, and further cultivating the suspension culture within the bioreactor vessel by providing the cell culture media to the bioreactor vessel for a second period of time while recovering the first portion of cultivated non-human animal cells and returning the second portion of cultivated non-human animal cells to the bioreactor vessel. Also, in one or more implementations, the series of acts 500 includes providing the cell culture media to the bioreactor vessel during the first period of time at a progressively increasing rate until a predetermined steady state rate and providing the cell culture media at the predetermined steady state rate during the second period of time.

In some implementations, the series of acts 500 also includes removing the measure of suspension culture from the bioreactor vessel at a continuous rate during the second period of time. In addition, in one or more implementations, the series of acts 500 further comprises recovering the first portion of cultivated non-human animal cells from the removed measure of suspension culture at a progressively decreasing recovery rate while returning the second portion of cultivated non-human animal cells to the bioreactor vessel at a respectively increasing retention rate.

In some implementations, the series of acts 500 includes separating the removed measure of suspension culture into a concentrated cell culture and a culture broth with cells removed and recovering the first portion of cultivated non-human animal cells from a respective portion of the concentrated cell culture of the removed and separated measure of suspension culture. In one or more implementations, the series of acts 500 further comprises removing spent cell culture media from the respective portion of the concentrated cell culture to recover the first portion of cultivated non-human animal cells. In some implementations, the series of acts 500 further comprises processing the culture broth for reintroduction into the bioreactor vessel to further cultivate the non-human animal cells therein and returning the processed culture broth to the bioreactor vessel.

As shown in FIG. 6, a series of acts 600 includes an act 602 of growing non-human animal cells in a suspension culture within a bioreactor for a first period of time, an act 604 of cultivating the suspension culture within the bioreactor for a second period of time. As also shown in FIG. 6, the act 604 includes an act 606 of providing cell culture media to the bioreactor for the second period of time, an act 608 of drawing a measure of the non-human animal cells from the bioreactor during the second period of time, and an act 610 of returning a first portion of the drawn measure of non-human animal cells to the bioreactor while providing the cell culture media.

In some implementations, the series of acts 600 further comprises growing the non-human animal cells within the bioreactor for the first period of time by providing cell culture media to the bioreactor until the non-human animal cells reach a target cell density within the suspension culture. In one or more implementations, the series of acts 600 also includes removing suspension culture from the bioreactor during the second period of time, separating the removed suspension culture into a concentrated cell culture and a culture broth with cells removed, and returning at least a portion of the culture broth with cells removed to the bioreactor during the second period of time.

In one or more implementations, the series of acts 600 further comprises maintaining a threshold cell density of the non-human animal cells within the suspension culture during the second period of time by continuously returning the first portion of the drawn measure of non-human animal cells to the bioreactor while recovering a second portion of the drawn measure of non-human animal cells. Also, in some implementations, the series of acts 600 includes progressively increasing a retention rate of returning the first portion of the drawn measure of non-human animal cells to the bioreactor during the second period of time.

Figure 7A:
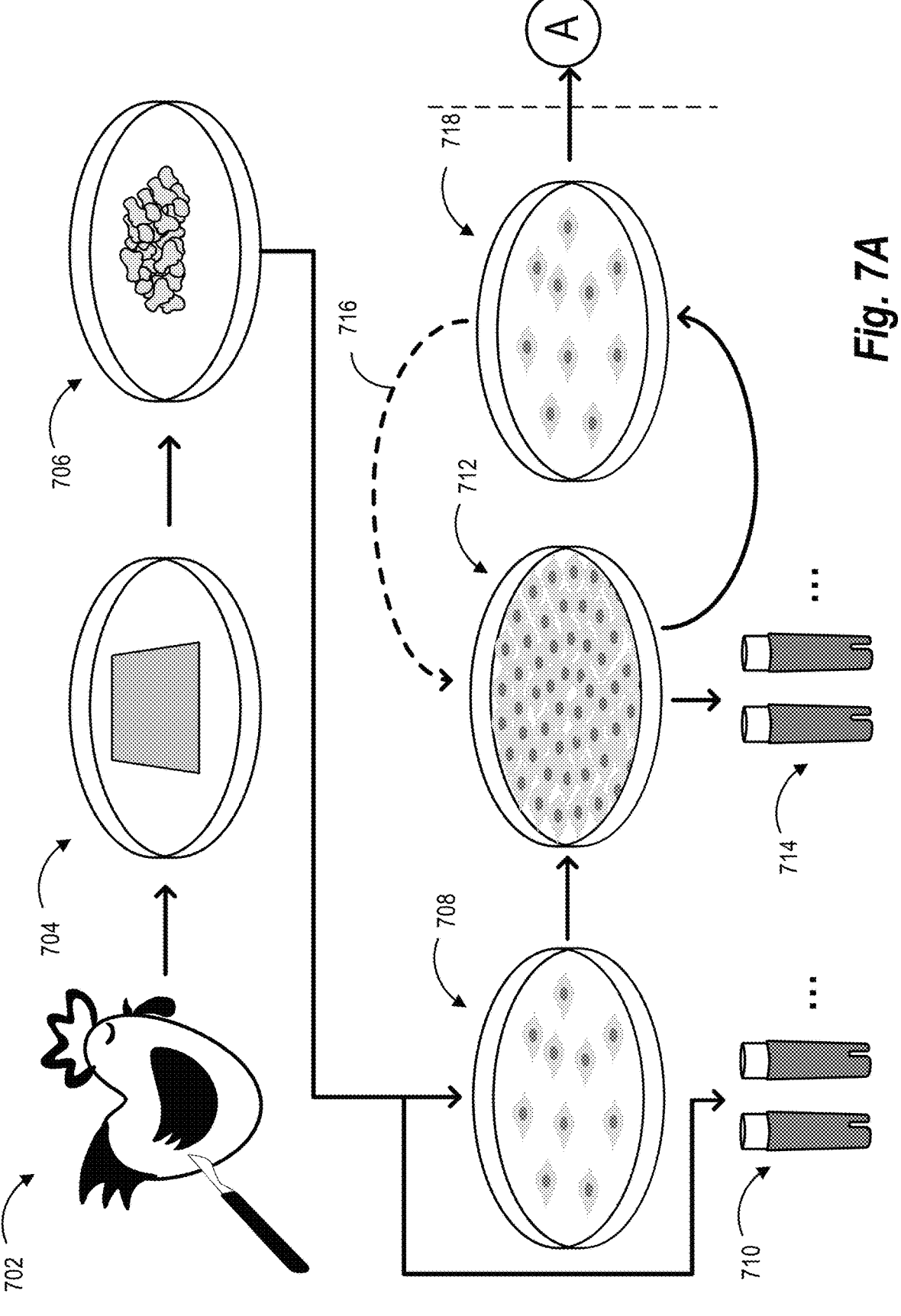
FIGS. 7A-7C illustrate a sequence diagram of growing and processing different types of comestible meat cells in accordance with one or more embodiments of the present disclosure.
Figure 7B:
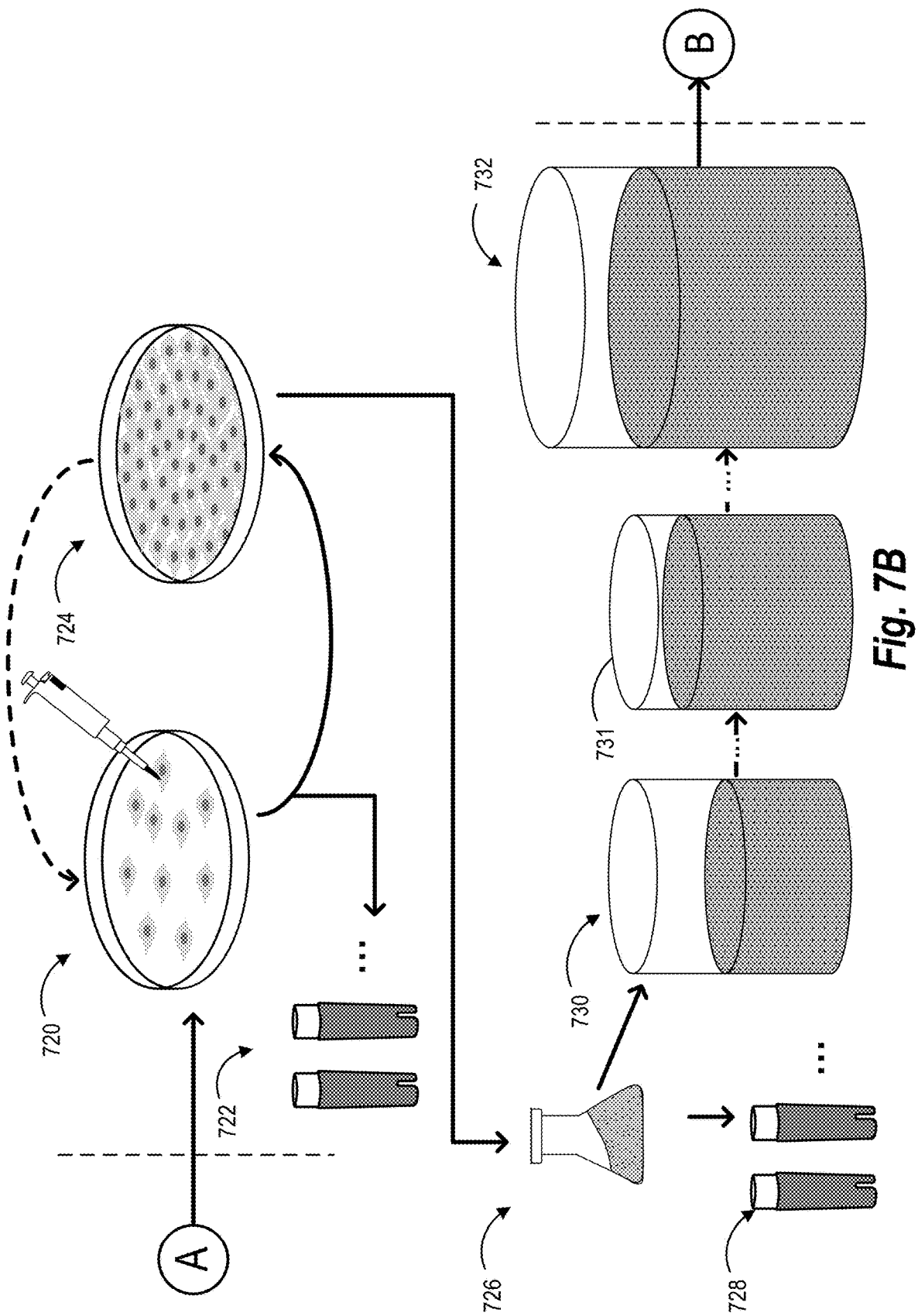
Figure 7C:
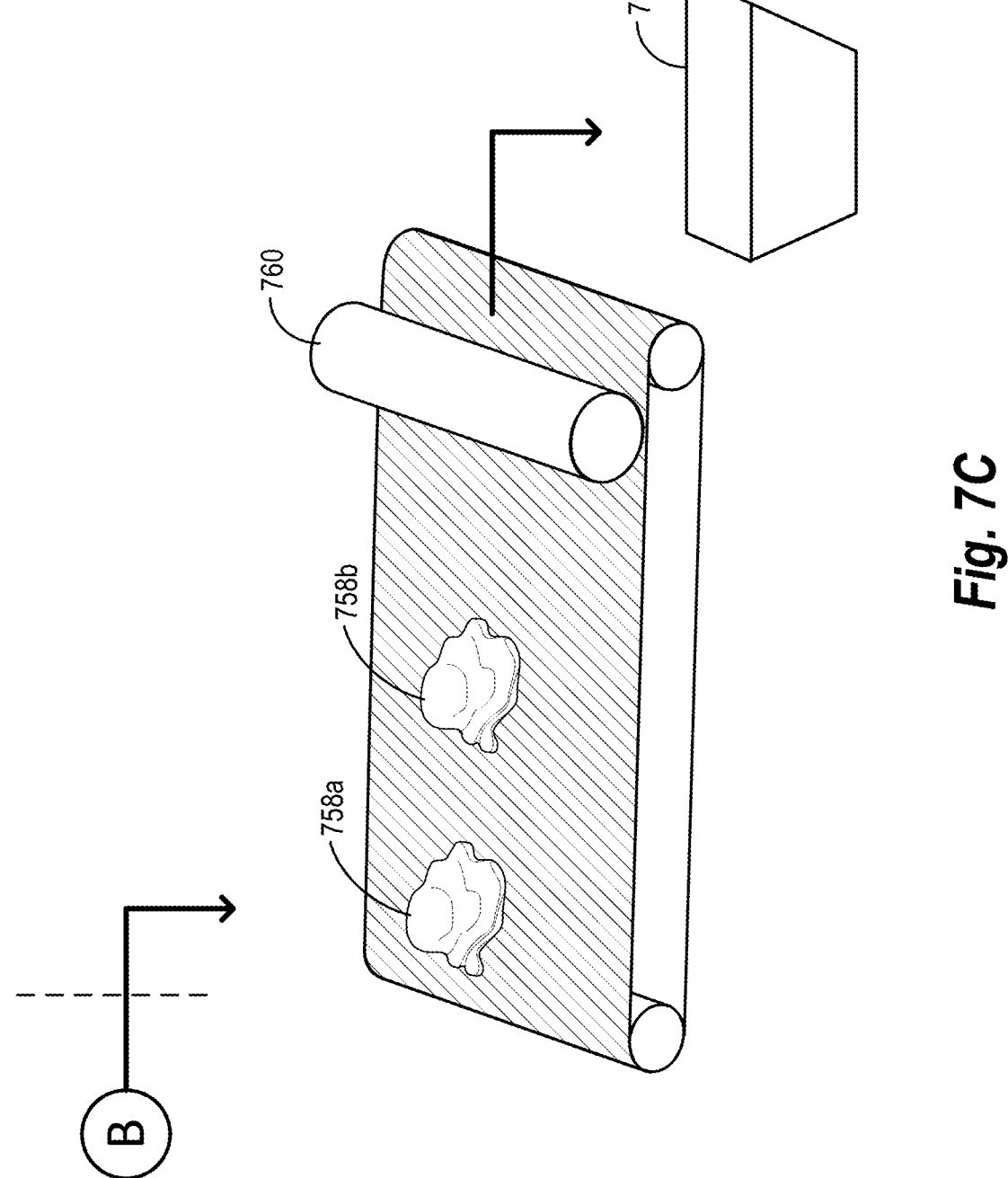

The paragraphs above describe systems, apparatuses, and methods for producing comestible non-human animal cells. FIGS. 7A-7C and the following accompanying paragraphs describe procurement of cells, cultivation of cells in suspension, and growth of cells into a cell mass in accordance with one or more implementations. Generally, FIGS. 7A-7C illustrate a process of collecting cells from an animal, growing cells in a favorable environment, banking successful cells, and collecting cells into a cell mass followed by de-wetting and/or other treatments.

As illustrated by step 702 in FIG. 7A, tissue is collected from a living animal via biopsy. In particular, stem cells, mesenchymal progeny, ectoderm lineage, and/or endoderm lineages can be isolated from the removed tissue. In some implementations of the present disclosure, tissue, such as fat and others, are processed to isolate stem cells, mesenchymal, ectoderm, and/or endoderm progeny or lineage cells. As illustrated, tissue 704 is removed from an animal. In some examples, the tissue 704 is removed from a living animal by taking a skin sample from the living animal. For instance, skin or muscle samples may be taken from a chicken, cow, fish, shellfish or another animal.

Cells may be extracted from the tissue 704 that was removed from the animal. More specifically, the tissue 704 is broken down by enzymatic and/or mechanical means. To illustrate, FIG. 7A includes digested tissue 706 that comprises the cells to be grown in cultivation.

Cells in the digested tissue 706 may be proliferated under appropriate conditions to begin a primary culture. As illustrated in FIG. 7A, cells 708 from the digested tissue 706 are spread on a surface or substrate and proliferated until they reach confluence. As shown in FIG. 7A, in some cases, cells 712 have reached confluence when they start contacting other cells in the vessel, and/or have occupied all the available surface or substrate.

In some examples, cells are stored and frozen (i.e., banked) at different steps along the cell culture process. Cryopreservation generally comprises freezing cells for preservation and long-term storage. In some implementations, tissue and/or cells are removed from a surface or substrate, centrifuged to remove moisture content, and treated with a protective agent for cryopreservation. For example, as part of cryopreservation, tissues and cells are stored at temperatures at or below-80C. The protective agent may comprise dimethyl sulfoxide (DMSO) or glycerol.

Cells stored through cryopreservation may be used to replenish working cell stock. For instance, while a portion of the digested tissue 706 is used as the cells 708 spread on a surface or substrate, the remaining or excess digested tissue 706 is transferred to cryovials 710 for storage. Furthermore, the cells 712 may be banked once reaching confluence and stored in cryovials 714.

Once the cells 712 have reached confluence, or just before the cells 712 have reached confluence (e.g., occupation of about 80% of the substrate), the disclosed process comprises a series of cell passage steps. During cell passage, the cells 712 are divided into one or more new culture vessels for continued proliferation. To illustrate, the cells 712 may be diluted or spread on one or more surfaces or substrates to form the cells 718. The cells 718 are then grown 716 to confluence, or just before confluence.

The cycle of dividing the cells 712 into the cells 718 for continued proliferation in new culture vessels may be repeated for a determined number of cycles. Typically, cell lines derived from primary cultures have a finite life span. Passaging the cells allows cells with the highest growth capacity to predominate. In one example, cells are passaged for five cycles to meet a desired genotypic and phenotypic uniformity in the cell population.

In some implementations, the disclosed method comprises immortalizing cells that have been grown and passaged for the determined number of cycles. For instance, the cells 718 may be immortalized. As shown in FIG. 7B, cells 720 have demonstrated a preferred growth capacity to proceed to immortalization. To achieve immortalization, the disclosed process transfects the cells 720 with genes of interest. In one example telomerase reverse transcriptase (TERT) is introduced to the cells 720. In some implementations, the cells may be subjected to a selection process as known by those skilled in the art. The cells 720 may then be passaged for a predetermined set of passaging cycles. In one example passaging cycle, the cells 720 are grown to (or near) confluence 724, then they are reseeded in new growth vessels, preserved in vials 722, or some combination of both. The disclosed process may include any number of passaging cycles to ensure that the cells have reached immortality (e.g., can passage 60+ times without senescing), a target growth capacity, and/or a target quantity for banking. For example, cells may be passaged until they have reached a passage level of 100 (e.g., have been passaged for 100 passaging cycles). In another example, cells are passaged until they reach a population doubling level of 100.

Cells that have reached immortality or a target growth capacity by living through a target passage level may be adapted to suspension culture. In one example, a suspension culture media and agitation of cells in this suspension environment help cells to adapt and start proliferating in the new growth environment. The cells adapted to suspension 726 may be stored in cryovials 728 for cryopreservation and banking. Cells in suspension 726 will begin to proliferate and the process begins a series of dilute and expand steps.

During dilution and expansion, cells are moved from growth vessels into newer, and progressively larger, growth vessels. For example, cells in suspension 726 may begin in a single tube. The cells will proliferate and increase in cellular density. Once the cells have reached a target cell number (i.e., viable cell density (VCD) at desired volume), they are diluted and moved to a larger growth vessel. Optionally, the cells are banked in cryovials throughout expansion. For example, once cells in suspension reach a maximum VCD, the cells may begin to leave exponential growth due to overcrowding. After reaching a target density, the suspension cells may be transferred to a larger vessel 730 and diluted with additional media. The dilute-and-expand steps are repeated using progressively larger vessels (e.g., the vessel 731 and the vessel 732) and/or progressive dilution until the cells reach a production-ready volume. For example, cells may be production ready at about a 1,000-100,000 liter scale at 5 million cells per mL. The cells may be banked in cryovials at any of the dilution and expansion cycles.

As part of preparing cells to form cell-based food products, the cells grown in suspension in the vessel 732 (or one of the previous vessels 730 or 731) may be transferred to a suspension bioreactor system configured for continuous cultivation and partial recovery of suspended cells, according to one or more of the implementations described herein (e.g., in relation to FIGS. 1-6). Furthermore, as shown in FIG. 7C, cells recovered during continuous cultivation, and/or at the conclusion thereof, can be further processed to form a cell-based food product, such as by reducing moisture content in recovered cells and/or by forming (e.g., molding or extruding) the harvested cells into cell masses resembling a patty, a filet, etc. To illustrate, FIG. 7C shows a pressure apparatus 760 that compresses cell masses 758a and 758b (e.g., masses of recovered cells).

While FIG. 7C illustrates a mechanical method for adjusting the moisture content and overall shape of the cell masses 758a and 758b, other methods may be used. For example, the cell masses 758a and 758b may be mixed with a drying agent, vacuum dried/compressed, further centrifuged, or otherwise processed. Each moisture adjusted and/or formed cell mass may be transferred to a container 762 for additional processing. For example, the cell masses 758a and 758b may be mixed with other food products, such as plant-based products, additional cell-based products, or other comestible ingredients, to modify a texture, color, flavor, and/or mass of the resultant cell-based food product.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various implementations of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various implementations of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to implementations containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to implementations containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absent a showing that the terms "first," "second," "third," etc., connote a specific order, these terms should not be understood to connote a specific order. Furthermore, absent a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art and are to be construed as being without limitation to such specifically recited examples and conditions. Although implementations of the present disclosure have been described in detail, it should be understood that the various changes, substitutions, and alterations could be made hereto without departing from the spirit and scope of the present disclosure.

The present invention may be embodied in other specific forms without departing from its spirit or essential characteristics. Indeed, the described implementations are to be considered in all respects only as illustrative and not restrictive. For example, the methods described herein may be performed with less or more steps/acts or the steps/acts may be performed in differing orders. Additionally, the steps/acts described herein may be repeated or performed in parallel to one another or in parallel to different instances of the same or similar steps/acts. The scope of the invention is, therefore, indicated by the appended claims rather than by the foregoing description. All changes that come within the meaning and range of equivalency of the claims are to be embraced within their scope.

What is claimed is:

1. A method for producing comestible non-human animal cells, the method comprising:
   cultivating suspension culture comprising non-human animal cells in a bioreactor vessel;
   removing a measure of the suspension culture from the bioreactor vessel while providing cell culture media to the bioreactor vessel;
   separating the removed measure of the suspension culture into a concentrated cell culture and a culture broth with cells removed;
   recovering a first portion of the concentrated cell culture for harvest concurrent with returning a second portion of the concentrated cell culture to the bioreactor vessel without returning the first portion to the bioreactor vessel; and
   processing cultivated non-human animal cells from the first portion of the concentrated cell culture to produce a cell-based food product.

2. The method of claim 1, further comprising:
   initially cultivating the suspension culture by providing the cell culture media to the bioreactor vessel for a first period of time; and further cultivating the suspension culture within the bioreactor vessel by providing the cell culture media to the bioreactor vessel for a second period of time while:
   removing the measure of the suspension culture from the bioreactor vessel without removing the measure of the suspension culture from a sterile environment comprising the bioreactor vessel and additional system components;
   returning the second portion of the concentrated cell culture to the bioreactor vessel without removing the second portion from the sterile environment; and
   recovering the first portion of the concentrated cell culture from the sterile environment.

3. The method of claim 2, further comprising:
   providing the cell culture media to the bioreactor vessel during the first period of time at a progressively increasing rate until a predetermined steady state rate; and
   providing the cell culture media to the bioreactor vessel at the predetermined steady state rate during the second period of time.

4. The method of claim 2, further comprising removing the measure of suspension culture from the bioreactor vessel at a continuous rate during the second period of time.

5. The method of claim 4, further comprising recovering the first portion of the concentrated cell culture from the removed measure of the suspension culture at a progressively decreasing recovery rate while returning the second portion of the concentrated cell culture to the bioreactor vessel at a respectively increasing retention rate.

6. The method of claim 2, further comprising:
   separating the removed measure of the suspension culture into the concentrated cell culture and the culture broth with cells removed without removing the measure of suspension culture from the sterile environment.

7. The method of claim 1, further comprising removing spent cell culture media from the first portion of the concentrated cell culture to recover the cultivated non-human animal cells.

8. The method of claim 1, further comprising:
   processing the culture broth with cells removed for reintroduction into the bioreactor vessel to further cultivate the non-human animal cells therein; and
   returning the processed culture broth to the bioreactor vessel.

9. A method for producing comestible non-human animal cells, the method comprising:
   growing non-human animal cells in a suspension culture within a bioreactor for a first period of time; and
   cultivating the suspension culture within the bioreactor for a second period of time by:
      continuously providing cell culture media to the bioreactor for the second period of time;
      drawing a measure of the suspension culture from the bioreactor during the second period of time;
      separating the drawn measure of the suspension culture into a concentrated cell culture and a culture broth with cells removed;
      returning a first portion of the concentrated cell culture to the bioreactor while continuously providing the cell culture media; and
      recovering, during the second period of time, a second portion of the concentrated cell culture for harvest without returning the second portion to the bioreactor; and processing cultivated non-human animal cells of the second portion of the concentrated cell culture to produce a cell-based food product.

10. The method of claim 9, wherein growing the non-human animal cells within the bioreactor for the first period of time comprises providing cell culture media to the bioreactor, drawing and separating cell suspension culture from the bioreactor, returning concentrated cell culture to the bioreactor, and removing culture broth with cells removed until the non-human animal cells reach a target cell density within the suspension culture.

11. The method of claim 9, further comprising:

returning at least a portion of the culture broth with cells removed to the bioreactor during the second period of time.

12. The method of claim 9, further comprising maintaining a threshold cell density of the non-human animal cells within the bioreactor during the second period of time by continuously returning the first portion of the concentrated cell culture to the bioreactor while recovering the second portion of the concentrated cell culture.

13. The method of claim 12, further comprising progressively increasing a retention rate of returning the first portion of the concentrated cell culture to the bioreactor during the second period of time.

14. The method of claim 9, further comprising:

processing the culture broth with cells removed for reintroduction into the bioreactor to further cultivate the non-human animal cells therein; and returning the processed culture broth to the bioreactor.

15. The method of claim 9, further comprising:

recovering, utilizing a cell concentration device, cultivated non-human animal cells from the second portion of the concentrated cell culture; and removing, utilizing the cell concentration device, spent cell culture media from the second portion of the concentrated cell culture.

16. The method of claim 15, further comprising diluting the second portion of the concentrated cell culture prior to removing the spent cell culture media.

17. The method of claim 15, further comprising preventing backflow contamination between the cell concentration device and lines back to the bioreactor.

18. The method of claim 17, wherein preventing backflow contamination between the cell concentration device and the lines back to the bioreactor comprises alternating use and sterilization of at least two parallel output lines of a sterile output module.

19. The method of claim 11, further comprising removing at least a second portion of the culture broth with cells removed as spent media.

20. The method of claim 9, further comprising utilizing a bypass line to enable decoupling of respective line distances, flow rates, and residence times between a first zone circulating the suspension culture at a higher flow rate and a second zone drawing the measure of the suspension culture at a lower flow rate.

\* \* \* \* \*